US006199436B1

(12) United States Patent
Morel et al.

(10) Patent No.: US 6,199,436 B1
(45) Date of Patent: Mar. 13, 2001

(54) METHOD AND APPARATUS FOR FIELD FLUID SAMPLING AND DISSOLVED GAS ANALYSIS

(75) Inventors: Oscar E. Morel; Nirmal Singh, both of Farmington Hills; Gerald E. McDonnell, Plymouth, all of MI (US)

(73) Assignee: Electric Power Research Institute, Inc., Palo Alto, CA (US)

( * ) Notice: Subject to any disclaimer, the term of this patent is extended or adjusted under 35 U.S.C. 154(b) by 0 days.

(21) Appl. No.: 09/328,689

(22) Filed: Jun. 9, 1999

(51) Int. Cl.[7] .................................................. G01N 1/10
(52) U.S. Cl. ............................................................ 73/864.52
(58) Field of Search ........................... 73/863.81, 863.83, 73/863.86, 864.43, 864.52, 864.73, 864.74, 864.91, 864.22, 864.23; 141/65

(56) References Cited

U.S. PATENT DOCUMENTS

| | | | |
|---|---|---|---|
| 4,046,013 | * | 9/1977 | Green .................................. 73/863.81 |
| 4,699,190 | * | 10/1987 | Bates ........................................ 141/65 |
| 4,927,605 | * | 5/1990 | Dorn et al. .......................... 73/864.23 |
| 5,131,283 | * | 7/1992 | Canfield .............................. 73/864.74 |
| 5,307,696 | * | 5/1994 | Allain et al. ....................... 73/864.74 |
| 5,313,969 | * | 5/1994 | Hsieh ...................................... 141/65 |
| 5,907,110 | * | 5/1999 | Garcia et al. ...................... 73/864.43 |

OTHER PUBLICATIONS

Jalbert, Jocelyn, et al., "Decomposition of Transformer Oils: A New Approach for the etermination of Dissolved Gases", IEEE Transactions on Power Delivery, vol. 12, No. 2, Apr. 1996.
EPRI Final Report EL–74880L, Nov. 1991.

* cited by examiner

Primary Examiner—Robert Raevis
(74) Attorney, Agent, or Firm—Flehr Hohbach Test Albritton & Herbert LLP

(57) ABSTRACT

A system and method for field fluid sampling and analyzing dissolved gases in electrical equipment fluids is described. The system includes a disposable vial which is sealed with a self-sealing stopper. Fluid to be analyzed is inserted into the vial by a hollow needle. Also described is apparatus for evacuating and sealing the vial and apparatus for introducing fluid from electrical equipment into the vial.

7 Claims, 4 Drawing Sheets

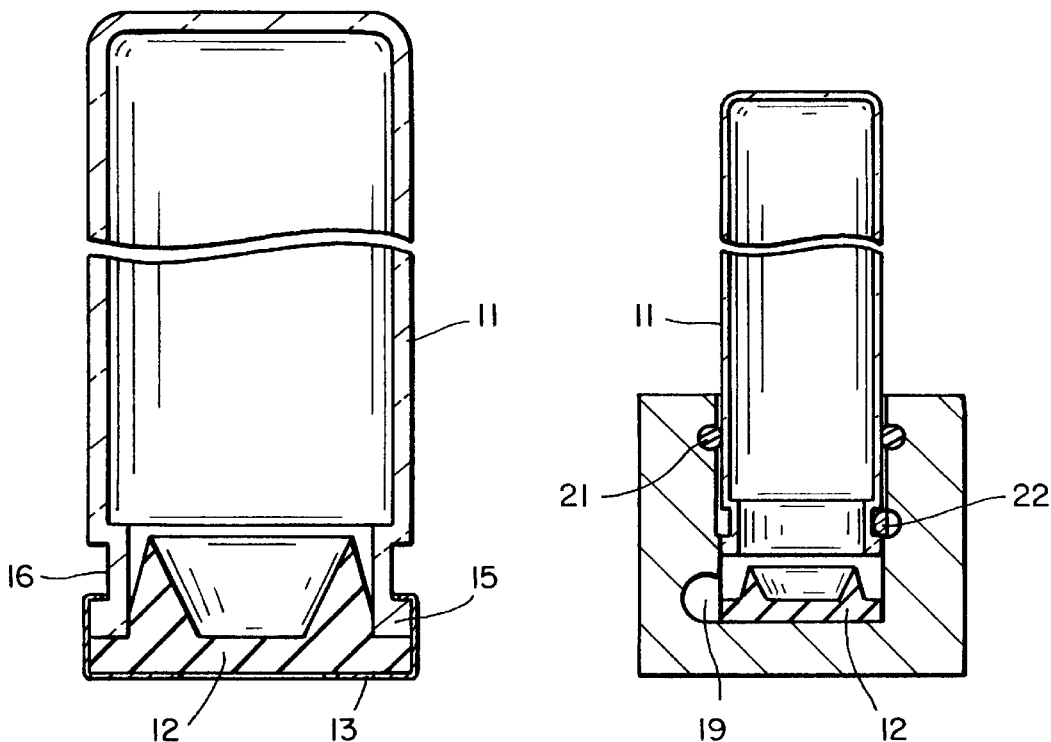
FIG_1   FIG_3
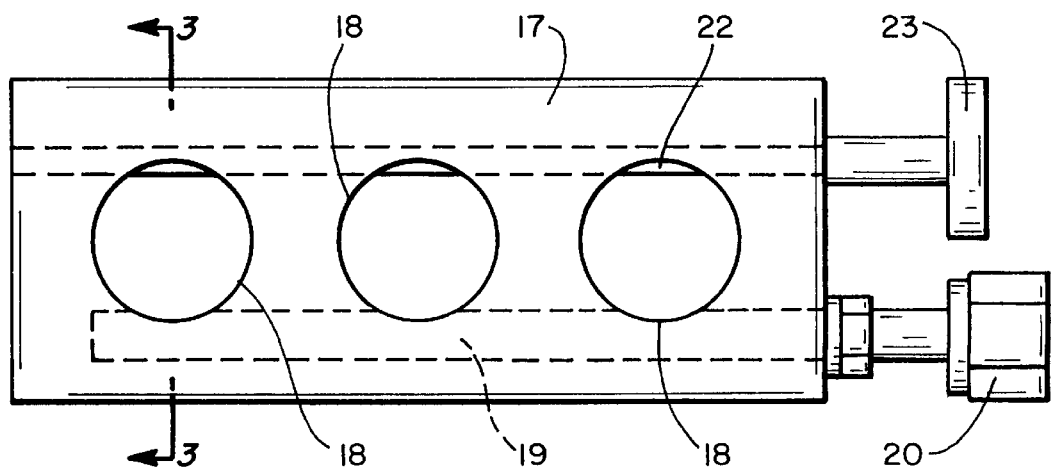
FIG_2

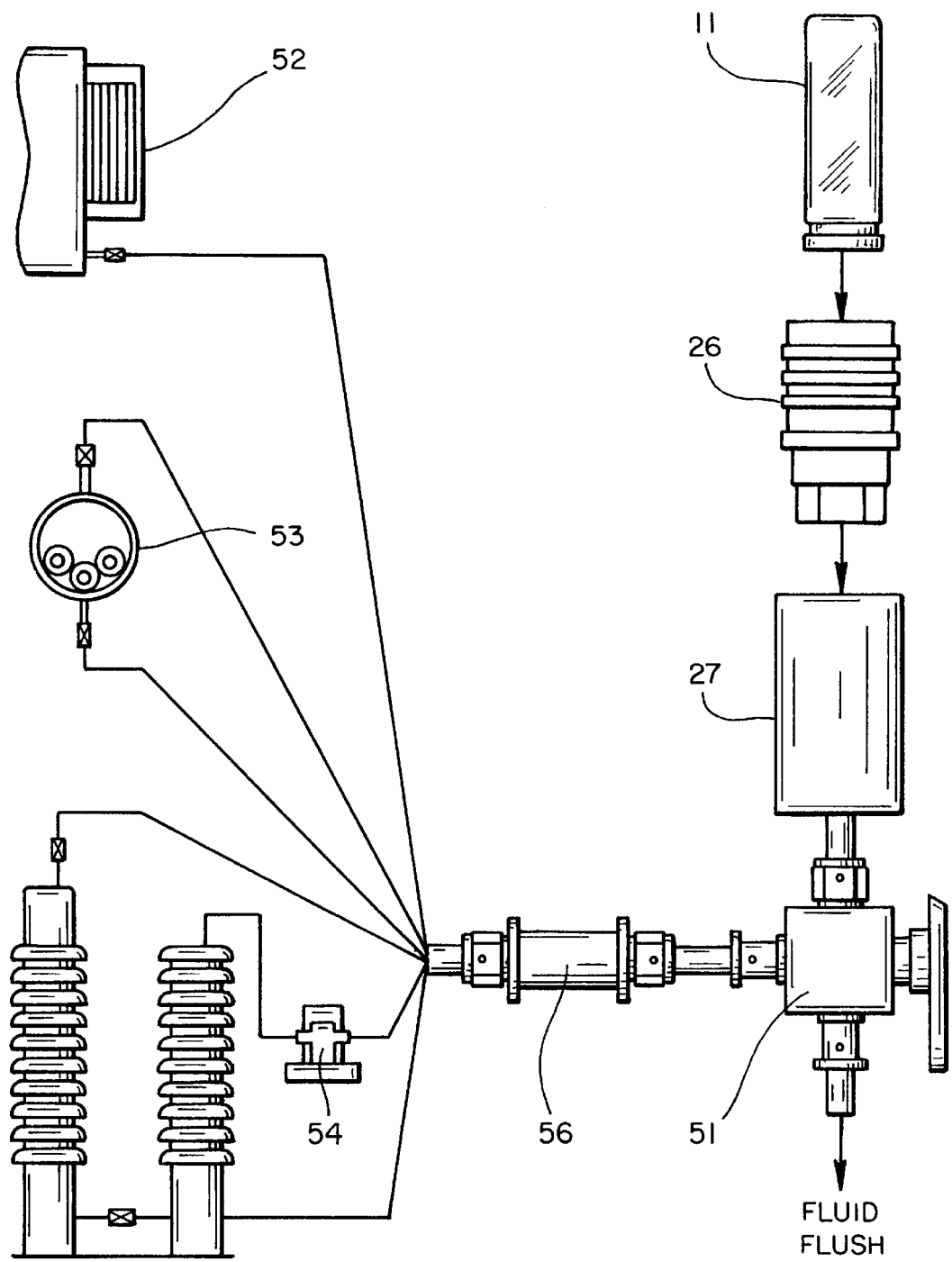
FIG_4

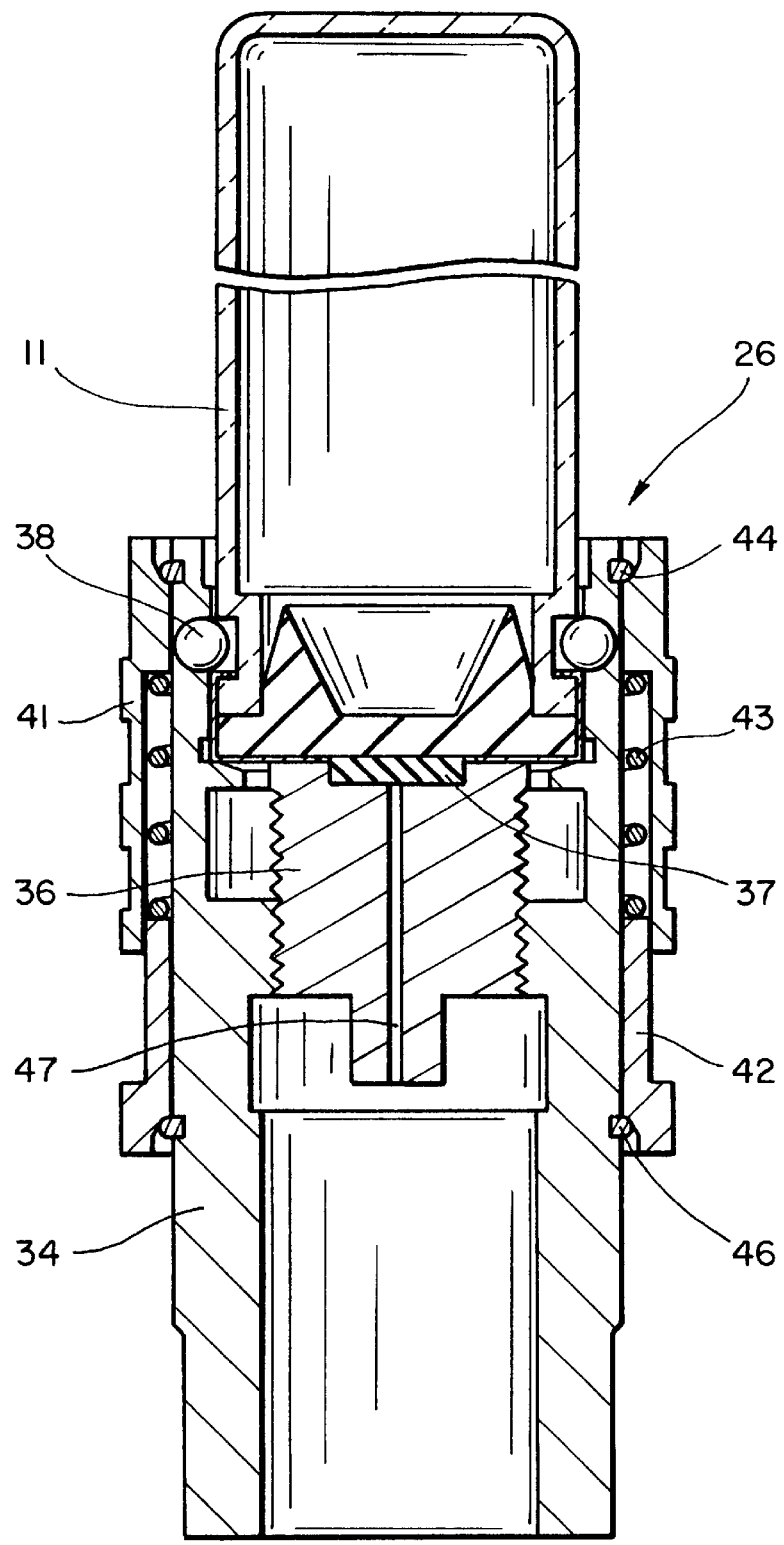
FIG_5

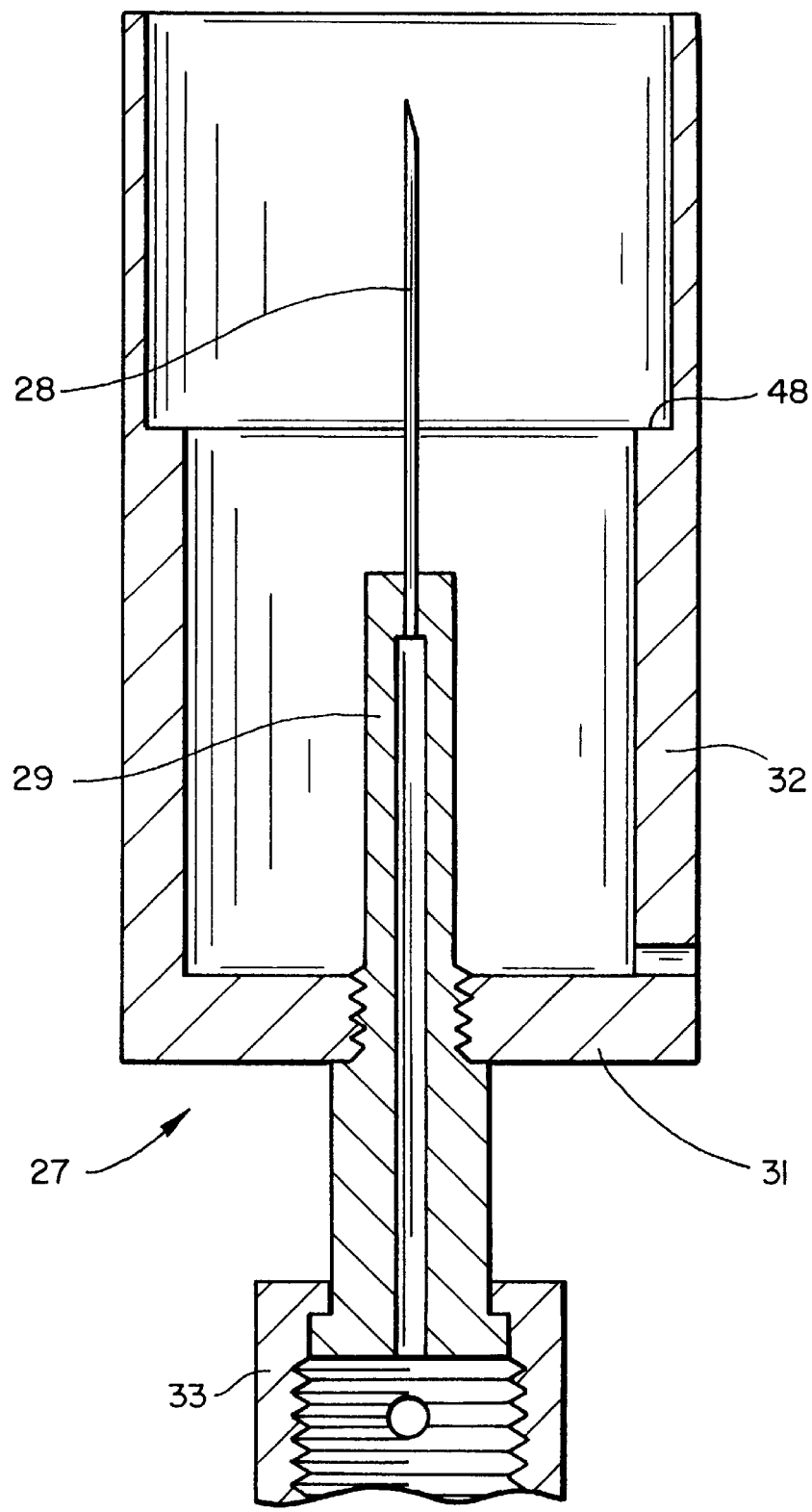
FIG_6

METHOD AND APPARATUS FOR FIELD FLUID SAMPLING AND DISSOLVED GAS ANALYSIS

BRIEF DESCRIPTION OF THE INVENTION

The present invention relates generally to a method and apparatus for field fluid sampling and dissolved gas analysis utilizing an evacuated disposable sampling vial, and to ancillary apparatus for vial evacuation and field fluid sampling.

BACKGROUND OF THE INVENTION

Fluid-filled equipment, which includes transformers, cables, bushings, terminations and circuit breakers, is an integral part of the electrical system. This diverse equipment represents considerable utility investment and a high proportion of it is advancing in age. About 30% of the high pressure fluid-filled transmission cable systems, the predominant form of U.S. underground transmission, are over 25 years old. Likewise, about 35% of the power transformers are over 30 years old. The rapidly emerging utility business climate dictates efficient use of such assets. Among other measures, this dictates proper periodic maintenance. The assessment of the condition of fluid-filled equipment through traditional evaluations of a fluid sample (dielectric breakdown, dissipation factor and color, etc.) has been made since the introduction of such equipment. This does not lead to reliable results for in-service fluids, although these tests are most appropriate for the selection and evaluation of new dielectric fluids. To enhance the value of periodic fluid testing, newer tests such as Dissolved Gas Analysis (DGA) and furfural content have been increasingly applied to fluid-filled equipment, with promising results.

The conventional method relating to the dissolved gas analysis of oil-filled electrical equipment is described in ASTM D3612. As a first step of the analysis, the oil sample is taken from a service cable with a glass syringe or a stainless steel cylinder and eventually brought to the laboratory where the gases are extracted from the oil under vacuum. In the second step, the extracted gas is collected in a second glass syringe and then taken to a gas chromatograph for the determination of individual component gases. While this procedure seems to serve well, it has several drawbacks, and it cannot be automated to increase sample throughput. The introduction of a second glass syringe contributes to the overall experimental error. The sampling of gas from the extraction apparatus and its subsequent injection to the gas chromatograph contributes to overall experimental error.

More recently, a method of analysis in which the gases in the head space of a vial are analyzed has been developed. In this approach, both the fluid sampling and analysis are performed in the same vial, leading to reduced sample manipulation and consequent enhanced accuracy and precision. This method is described in *EPRI Final Report* EL-7488-L, November, 1991. While the prior art system has many advantages and has served the industry well, the time required to assemble, disassemble and clean the cells, despite an efficient cleaning system involving a vapor degreaser, adds to the cost of analysis. The analysis cells are large, heavy and expensive. Shipping containers are heavy and add to the cost of shipping the samples for analysis.

OBJECTS AND SUMMARY OF THE INVENTION

It is a general object of the present invention to provide an improved field fluid sampling and dissolved gas analysis system.

It is a further object of the present invention to provide a small disposable glass sampling vial which can be maintained at an appropriate vacuum, and the sample fluid introduced into the vial through a self-sealing stopper by a hollow needle.

It is another object of the present invention to provide a system for evacuating the disposable vial and applying a self-sealing stopper.

It is a further object of the present invention to provide an adapter incorporating a needle for receiving the vial, and for introduction of fluid samples into the vial.

It is a further object of the present invention to provide an easy-to-use, inexpensive, accurate oil sampling system in which a disposable vial serves the dual function of fluid collection and subsequent dissolved gas analysis.

It is a further object of the present invention to provide an oil sampling system capable of operating in field conditions on a consistent basis with all types of fluid-filled equipment and in all types of weather.

The foregoing and other objects of the invention are achieved by a system in which a disposable vial is inserted in an evacuation and sealing system where it is evacuated and sealed with a self-sealing stopper. The sealed, evacuated vial is then inserted in an adapter where a needle penetrates the stopper to introduce sample fluid into the vial. The stopper reseals when the needle is removed, the gases in the vial are analyzed, and the vial is then disposed.

BRIEF DESCRIPTION OF THE DRAWINGS

The invention will be more clearly understood from the following description when read in conjunction with the accompanying drawings in which:

FIG. 1 shows an evacuated disposable sample vial.

FIG. 2 is a top plan view of a vial sealing and evacuation system.

FIG. 3 is a sectional view taken generally along the line 3—3 of FIG. 2 with a vial and stopper in place.

FIG. 4 is a schematic diagram showing a fluid sampling assembly.

FIG. 5 is a cross-sectional view of the vial coupler of FIG. 4.

FIG. 6 is a cross-sectional view of the needle assembly of FIG. 4.

DESCRIPTION OF PREFERRED EMBODIMENT

Referring to FIG. 1, a transparent evacuated disposable 20 ml crimp-top headspace vial 11 is sealed with a rubber stopper 12, inserted into the open end, and held by a crimp cap 13 which extends over the stopper and over the edge of the rim 15 into the neck 16. The stopper material should have low gas permeability, good resilience, and compatibility with hydrocarbon fluids. The most important characteristic is low gas permeability which determines the time the vial can maintain a proper vacuum. The vacuum assures that a minimal concentration of oxygen and nitrogen are in the vial prior to introducing a sample. After sampling, the stopper must contain the gases from the fluid until an analysis of the gases is performed. The stopper material needs to enable the penetration of a hollow needle through which the sample fluid can be introduced into the evacuated vial and which is self-healing or -sealing when the sampling needle is removed.

The time lag for gas diffusion through a rubbery material can be estimated from $$\theta = \frac{l^2}{6D}$$

where θ is the time lag, l is the membrane thickness, and D is the gas diffusivity. While the nature of the material can be selected to minimize the value of D, the design can have a greater impact by an increase in the stopper thickness l. Several stopper materials and designs were considered so that they not only held the vacuum in the cell or vial, but also lent themselves to the introduction of the fluid sample into this cell or vial. This necessitated materials with the lowest permeability and ability to perform satisfactorily in winter. The materials tested included: silicones, butyl rubbers, polyacrylics, chloroprenes and fluoroelastomers. While polyacrylic stoppers proved very promising, this material was found to be less resilient than the halobutyl rubber, as small leaks were observed after pulling the needle away from the septum at the end of the sampling process. Stopper wall thicknesses ranging from 120 mils to 160 mils were investigated. However, the choice of 120 mils was discovered to be the most appropriate in the form of halobutyl material. It was discovered that the confinement of the gases in the vial was greatly enhanced if the cells were maintained upside-down, after the fluid sample was taken. The reason for this simple expedient lies in the fact that the gas concentration of low molecular components in the liquid phase is considerably lower than the corresponding concentration in the gas phase. As a consequence, the possible migration of gases out of the cell is reduced when the fluid is in contact with the stopper instead of the gas.

The disposable glass vial 11 is evacuated and sealed with a stopper in the system shown in FIGS. 2 and 3. The system includes a body 17 with wells 18 which receive the glass vials 11. The wells are connected to a manifold 19 which is connected to a molecular vacuum pump (not shown) by fitting 20. A vacuum gage (not shown) is connected between the fitting 20 and the vacuum pump to monitor the vacuum pressure. O-ring 21 provides a seal when the glass vial 11 is inserted in a well 18. The glass vial is retained at the neck 16 during evacuation by a shaped retainer 22 which is rotated by lever 23. The rubber stopper 12 is placed at the bottom of the well prior to insertion of the vial. After a proper vacuum is applied, the lever 23 is rotated, releasing the retainer 22, and the vial is pushed down to seat the stopper. The vacuum is broken and the evacuated vial is then removed and the aluminum crimp cap 13 is applied. The vacuum inside the glass vial keeps the rubber stopper in place before the aluminum crimp cap is applied.

The sampling assembly shown in FIGS. 4, 5 and 6 facilitates sample fluid collection from associated electrical equipment. The assembly includes a quick disconnect vial coupler 26 adapted to hold the disposable sample vial 11. The coupler is used to couple the sample vial to the needle assembly 27, FIG. 6. The needle assembly or adapter 27 includes a needle 28 soldered to base 29 threaded to the bottom 31 of the cylindrical protective housing 32. A fitting 33 provides connection to the valve 51, FIG. 4.

The vial coupler 26, FIG. 5, includes a cylindrical member 34, which threadably receives a support 36, which supports a rubber septum 37, which is compressed against the face of the stopper 12 to provide an additional seal while the needle is retrieved after sampling. The resealing of the rubber stopper after retracting the needle is not instantaneous. The septum 37 helps to eliminate the ingress of air as the rubber stopper reseals itself. The glass vial is retained by engagement of ball bearings 38 with the neck 16. The coupler includes a spring assembly comprising telescoped cylindrical members 41 and 42, which are urged apart by a spring 43, and retained by retainers 44 and 46. When the coupler is inserted into the adapter, the needle 28 is guided by the opening 47 in the support 34. As the end of the needle reaches the septum, the member 42 strikes the ledge 48 in the adapter, and as the coupler is moved further into the adapter 27 the spring 43 is compressed. After the needle has penetrated the stopper and sample fluid has been injected into the vial, the spring helps in moving the coupler 26 out of the adapter 27.

FIG. 4 shows the sampling assembly connected to a three-way valve 51 which allows fluid flush before sampling. The valve is directly connected to the fluid-filled equipment, such as power transformers 52 and cables 53. The valve is also connected to a suitable pump 54 which is used to pump fluid from equipment filled with viscous fluid. Preferably, a filter 56 is inserted in line with the valve 51.

There has been described a new system for dissolved gas analysis of fluids in electrical equipment. The system includes a novel disposable crimp-top cell or vial for fluid sample collection and subsequent analysis. The system includes apparatus for evacuating and sealing the vial, and equipment for field sampling fluids in electrical equipment, and introducing the fluids into the evacuated vial. The disposable sampling cell or vial is sealed with a resealable rubber stopper. Fluid is introduced into the vial by a hollow needle which pierces the stopper.

The foregoing description of a specific embodiment of the present invention is presented for purposes of illustration and description. It is not intended to be exhaustive or to limit the invention to the precise form disclosed, obviously many modifications and variations are possible in view of the above teachings. The preferred embodiment was chosen and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents.

What is claimed is:

1. Kit for analyzing gases dissolved in a sample fluid comprising:

a disposable sample vial having an open end, a self-sealing stopper inserted into said open end to seal the vial, a crimp cap applied to the stopper and vial to maintain the seal on the vial, a coupler for slidably receiving the vial and securing the vial within the coupler, the coupler having a support, for a needle, with a septum to help eliminate the leakage of air into the vial, a spring assembly included with the coupler for assisting the coupler in disengaging an adaptor, the adapter including a hollow needle which follows the support in the coupler and penetrates the stopper for introducing sample fluid from fluid-filled electrical equipment into said vial whereby dissolved gases are captured in the vial for analysis, the spring assembly assists in removing the needle from the vial once the dissolved gases are captured.

2. Kit as in claim 1 including:

an evacuation system for receiving said vial and stopper, evacuating the vial and inserting the stopper and applying the crimp cap to provide an evacuated disposable vial for receiving the fluid sample.

3. Kit as in claim 2 in which the stopper material is resilient and has low gas permeability.

4. The method of analyzing dissolved gases in a fluid comprising the steps of:

preparing an evacuated disposable sample vial sealed with a self-sealing stopper and a crimp cap, introducing fluid sample from electrical equipment into said vial with a hollow needle which is inserted through a support and through a septum, into said vial through said self-sealing stopper, removing the vial with the aid of a spring, and transporting the vial containing the fluid sample to gas analyzing apparatus.

5. The method of claim 4 in which the vial is oriented during transport with the plug side down in order to maintain contact between the fluid and the stopper.

6. Kit as in claim 1 wherein the spring assembly further comprises telescoped cylindrical members and a spring.

7. Kit as in claim 6 wherein the cylindrical members are urged apart by the spring, and as the coupler moves into the adaptor the spring is compressed and the compressive force assists in removing the adaptor from the coupler.

* * * * *